(12) United States Patent
Ross et al.

(10) Patent No.: US 10,383,629 B2
(45) Date of Patent: Aug. 20, 2019

(54) SYSTEM AND METHOD FOR PREVENTING REPROCESSING OF A POWERED SURGICAL INSTRUMENT

(75) Inventors: Adam Ross, Prospect, CT (US); Michael Zemlok, Prospect, CT (US)

(73) Assignee: Covidien LP, Mansfield, MA (US)

(*) Notice: Subject to any disclaimer, the term of this patent is extended or adjusted under 35 U.S.C. 154(b) by 957 days.

(21) Appl. No.: 12/796,194

(22) Filed: Jun. 8, 2010

(65) Prior Publication Data

US 2011/0034910 A1 Feb. 10, 2011

Related U.S. Application Data

(60) Provisional application No. 61/232,582, filed on Aug. 10, 2009.

(51) Int. Cl.
| | |
|---|---|
| *A61B 17/00* | (2006.01) |
| *A61B 17/32* | (2006.01) |
| *A61B 17/072* | (2006.01) |
| *A61B 17/068* | (2006.01) |
| *G06F 19/00* | (2018.01) |
| *A61B 90/90* | (2016.01) |
| *A61B 90/00* | (2016.01) |

(52) U.S. Cl.
CPC ...... *A61B 17/07207* (2013.01); *A61B 17/068* (2013.01); *A61B 17/072* (2013.01); *G06F 19/00* (2013.01); *A61B 90/90* (2016.02); *A61B 2017/00398* (2013.01); *A61B 2017/00473* (2013.01); *A61B 2090/0803* (2016.02); *A61B 2090/0814* (2016.02)

(58) Field of Classification Search
None
See application file for complete search history.

(56) References Cited

U.S. PATENT DOCUMENTS

| | | | | |
|---|---|---|---|---|
| 5,077,506 | A * | 12/1991 | Krause | A61B 17/32002 318/67 |
| 5,209,235 | A * | 5/1993 | Brisken | A61B 5/117 600/466 |
| 5,391,144 | A * | 2/1995 | Sakurai | A61B 17/22012 601/3 |
| 5,400,267 | A * | 3/1995 | Denen et al. | 702/59 |

(Continued)

FOREIGN PATENT DOCUMENTS

| | | |
|---|---|---|
| EP | 0449256 A2 | 10/1991 |
| EP | 0 537 570 B1 | 4/1993 |

(Continued)

OTHER PUBLICATIONS

DS2460 SHA-1 Coprocessor with EEPROM (example tech specs from Dallas Semiconductir).*

(Continued)

*Primary Examiner* — Carl H Layno
*Assistant Examiner* — Manolis Pahakis (57) ABSTRACT

A surgical instrument is disclosed. The instrument includes a microcontroller coupled to a memory, the microcontroller is configured to control the surgical instrument and a usage counter stored in the memory that is incremented when the surgical instrument is activated, wherein the microcontroller is further configured to prevent actuation of the surgical instrument when the usage counter is above a predetermined threshold.

14 Claims, 6 Drawing Sheets

(56) References Cited

U.S. PATENT DOCUMENTS

| | | | |
|---|---|---|---|
| 5,425,375 A * | 6/1995 | Chin et al. .................... 600/549 |
| 5,433,721 A * | 7/1995 | Hooven ............... A61B 17/068 |
| | | | 227/175.1 |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,562,239 A | 10/1996 | Boiarski et al. |
| 5,667,517 A | 9/1997 | Hooven |
| 5,749,885 A * | 5/1998 | Sjostrom .......... A61B 17/32002 |
| | | | 604/22 |
| 5,792,138 A * | 8/1998 | Shipp ..................... A61B 18/12 |
| | | | 429/61 |
| 5,888,241 A * | 3/1999 | Jarvik .................. A61M 1/102 |
| | | | 417/254 |
| 6,090,123 A * | 7/2000 | Culp et al. .................... 606/180 |
| 6,165,169 A | 12/2000 | Panescu et al. |
| 6,166,538 A * | 12/2000 | D'Alfonso .................... 324/228 |
| 6,237,604 B1 | 5/2001 | Burnside et al. |
| 6,295,330 B1 * | 9/2001 | Skog et al. .................... 377/15 |
| 6,387,092 B1 | 5/2002 | Burnside et al. |
| 6,578,579 B2 | 6/2003 | Burnside et al. |
| 6,595,930 B2 * | 7/2003 | Rosenheimer ................ 600/561 |
| 6,611,793 B1 | 8/2003 | Burnside et al. |
| 6,675,031 B1 * | 1/2004 | Porges et al. ................. 600/322 |
| 6,792,390 B1 * | 9/2004 | Burnside et al. ............. 702/183 |
| 7,048,687 B1 | 5/2006 | Reuss et al. |
| 7,126,303 B2 * | 10/2006 | Farritor .................. A61B 1/041 |
| | | | 318/568.12 |
| 7,193,519 B2 | 3/2007 | Root et al. |
| 7,199,545 B2 * | 4/2007 | Oleynikov ............. A61B 1/041 |
| | | | 104/138.2 |
| 7,319,907 B2 * | 1/2008 | Kasdan .............. G01N 15/1456 |
| | | | 600/322 |
| 7,431,188 B1 | 10/2008 | Marczyk |
| 9,164,271 B2 * | 10/2015 | Ebata .................. G02B 23/2484 |
| 2002/0019596 A1 * | 2/2002 | Eggers ............... A61B 18/1482 |
| | | | 600/564 |
| 2002/0023223 A1 | 2/2002 | Schmidt et al. |
| 2002/0198554 A1 | 12/2002 | Whitman et al. |
| 2003/0106930 A1 | 6/2003 | Williams |
| 2003/0181934 A1 * | 9/2003 | Johnston ............... A61B 17/162 |
| | | | 606/167 |
| 2004/0059197 A1 * | 3/2004 | Yamashita ............. A61B 5/0002 |
| | | | 600/300 |
| 2004/0220577 A1 * | 11/2004 | Cragg ................. A61B 17/1617 |
| | | | 606/80 |
| 2004/0267340 A1 * | 12/2004 | Cioanta .................... A61F 7/123 |
| | | | 607/105 |
| 2005/0096684 A1 * | 5/2005 | Farrow ............ A61B 17/32002 |
| | | | 606/170 |
| 2006/0074405 A1 * | 4/2006 | Malackowski .... A61B 17/1613 |
| | | | 606/1 |
| 2006/0095096 A1 * | 5/2006 | DeBenedictis et al. ........ 607/88 |
| 2006/0129202 A1 * | 6/2006 | Armstrong ...................... 607/45 |
| 2006/0278681 A1 * | 12/2006 | Viola ............... A61B 17/07207 |
| | | | 227/176.1 |
| 2007/0032818 A1 | 2/2007 | McEwen et al. |
| 2007/0043272 A1 * | 2/2007 | Mannheimer et al. ........ 600/323 |
| 2007/0043398 A1 * | 2/2007 | Ternes et al. .................... 607/19 |
| 2007/0129684 A1 * | 6/2007 | Garbini et al. ................. 604/171 |
| 2008/0118890 A1 * | 5/2008 | Knopp ................. A61C 1/0015 |
| | | | 433/104 |
| 2008/0164296 A1 * | 7/2008 | Shelton et al. ............. 227/175.1 |
| 2008/0185419 A1 * | 8/2008 | Smith et al. ................ 227/179.1 |
| 2008/0251568 A1 * | 10/2008 | Zemlok ............... A61B 17/068 |
| | | | 227/175.1 |
| 2008/0255607 A1 * | 10/2008 | Zemlok .......................... 606/205 |
| 2008/0262305 A1 * | 10/2008 | Omoto ............... A61B 1/00006 |
| | | | 600/118 |
| 2009/0018566 A1 * | 1/2009 | Escudero ....... A61B 17/320758 |
| | | | 606/159 |
| 2009/0018624 A1 * | 1/2009 | Levinson et al. .............. 607/96 |
| 2009/0090763 A1 * | 4/2009 | Zemlok ............ A61B 17/07207 |
| | | | 227/175.2 |
| 2009/0143797 A1 * | 6/2009 | Smith ................ A61B 17/1285 |
| | | | 606/169 |
| 2009/0177139 A1 | 7/2009 | Boyden et al. |
| 2009/0182207 A1 * | 7/2009 | Riskey et al. ................. 600/302 |
| 2009/0206136 A1 * | 8/2009 | Moore ............. A61B 17/07207 |
| | | | 227/176.1 |
| 2009/0234232 A1 * | 9/2009 | Gertsen ................ A61B 8/4461 |
| | | | 600/459 |
| 2009/0326569 A1 * | 12/2009 | Tanaka ........... A61B 17/320068 |
| | | | 606/169 |
| 2010/0076474 A1 * | 3/2010 | Yates et al. .................... 606/170 |
| 2010/0125292 A1 * | 5/2010 | Wiener ............. A61B 17/32006 |
| | | | 606/169 |
| 2011/0017801 A1 * | 1/2011 | Zemlok ............. A61B 17/07207 |
| | | | 227/175.1 |
| 2011/0148646 A1 * | 6/2011 | Ko .......................... A61B 17/00 |
| | | | 340/679 |
| 2011/0208170 A1 * | 8/2011 | Hafner ..................... A61B 17/00 |
| | | | 606/1 |
| 2011/0218522 A1 * | 9/2011 | Whitman ........................ 606/1 |
| 2011/0301611 A1 * | 12/2011 | Garcia ................. A61B 17/162 |
| | | | 606/80 |
| 2013/0203014 A1 * | 8/2013 | Lieb ........................ A61C 1/185 |
| | | | 433/131 |
| 2015/0257970 A1 * | 9/2015 | Mucke ................ A61N 1/0476 |
| | | | 601/21 |

FOREIGN PATENT DOCUMENTS

| | | |
|---|---|---|
| EP | 0 647 431 B1 | 4/1995 |
| EP | 0 738 501 A1 | 10/1996 |
| EP | 1 201 196 A1 | 5/2002 |
| EP | 1201196 A1 | 5/2002 |
| EP | 1 658 817 A1 | 5/2006 |
| EP | 1658817 A1 | 5/2006 |
| EP | 1 769 754 | 4/2007 |
| EP | 1943958 A1 | 7/2008 |
| FR | 2 849 589 A1 | 7/2004 |
| FR | 2849589 A1 | 7/2004 |
| JP | 2001-255953 A | 9/2001 |
| JP | 3-276345 B2 | 4/2002 |
| JP | 2003-272009 A | 9/2003 |
| JP | 2004-093693 A | 3/2004 |
| JP | 2007-318669 A | 12/2007 |
| JP | 2008-010952 A | 1/2008 |
| WO | 94/14129 A1 | 6/1994 |
| WO | WO 94/14129 A1 | 6/1994 |
| WO | WO 00/72765 A1 | 12/2000 |
| WO | WO 03/026511 | 4/2003 |
| WO | WO 2003/026511 | 4/2003 |
| WO | 2007/014355 A2 | 2/2007 |
| WO | WO 2007/014355 A2 | 2/2007 |
| WO | 2007/114868 A2 | 10/2007 |
| WO | WO 2007/114868 A2 | 10/2007 |
| WO | 2008/137813 A1 | 11/2008 |

OTHER PUBLICATIONS

Dallas Semiconductor Corp., DS2434 Battery Identification Chip, 1995.*

Aresco Inc., Have you ever wondered what the motor nameplate information means?, ARESCO Technical Bulletin vol. 1, No. 1 Jun. 1998.*

European Search Report for EP 10251416.3-2310 date of completion is Mar. 3, 2011 (4 pages).

European Search Report dated Apr. 17, 2007 for Corresponding Patent Application EP06026840.

International Search Report for corresponding PCT Application—PCT/US06/21524—dated May 28, 2008 (4 Pages).

Detemple, P., "Microtechnology in Modern Health Care", Med Device Technol. 9(9):18-25 (1998).

European Search Report for corresponding EP 08252703.7 dated Oct. 31, 2008 (3 pages).

(56) References Cited

OTHER PUBLICATIONS

European Search Report dated Feb. 27, 2009 for Corresponding Patent Application 08253184.9.
European Search Report for Corresponding EP 08251357 dated Sep. 29, 2009 (3 pages).
European Search Report dated Jul. 28, 2011 for EP 11 15 2266.
Japanese Office Action corresponding to counterpart Int'l Appln. No. JP 2010-174054 dated Dec. 7, 2015 (with English Translation).
European Office Action corresponding to counterpart Int'l Application No. EP 10 251 416.3 dated Dec. 14, 2015.
Australian Patent Examination Report No. 1 corresponding to counterpart Application No. AU 2014250697 dated Sep. 9, 2015.
European Office Action corresponding to counterpart Int'l Application No. EP 10 25 14 16.3 dated Jul. 6, 2016.
Canadian Office Action corresponding to counterpart Int'l Application No. CA 2,709,747 dated Jul. 8, 2016.
Canadian Office Action issued in corresponding Canadian Application No. 2,709,747 dated Nov. 18, 2016.
Canadian Office Action corresponding to counterpart Int'l Appln. No. CA 2,709,747 dated Jul. 10, 2017.

\* cited by examiner

SYSTEM AND METHOD FOR PREVENTING REPROCESSING OF A POWERED SURGICAL INSTRUMENT

CROSS REFERENCE TO RELATED APPLICATION

The present application claims the benefit of and priority to U.S. Provisional Application Ser. No. 61/232,582 filed on Aug. 10, 2009, the entire contents of which are incorporated herein by reference.

BACKGROUND

Technical Field

The present disclosure relates to a surgical instrument. More particularly, the present disclosure relates to a surgical instrument which includes a mechanism for preventing reprocessing of the instruments and components thereof.

Background of Related Art

Current known devices can typically require 10-60 pounds of manual hand force to clamp tissue and deploy and form surgical fasteners in tissue which, over repeated use, can cause a surgeon's hand to become fatigued. Gas powered pneumatic staplers which implant surgical fasteners into tissue are known in the art. Certain of these instruments utilize a pressurized gas supply which connects to a trigger mechanism. The trigger mechanism, when depressed, simply releases pressurized gas to implant a fastener into tissue.

Motor-powered surgical staplers are also known in the art. These include powered surgical staplers having motors which activate staple firing mechanisms. However, these motor powered devices only provide for limited user control of the stapling process. The user can only toggle a single switch and/or button to actuate the motor and applies corresponding torque to the stapler's firing mechanisms. In certain other devices, a controller is used to control the stapler.

There is a continual need for new and improved powered surgical staplers which include various sensors. The sensors provide relevant feedback to feedback controllers which automatically adjust various parameters of the powered stapler in response to sensed feedback signals representative of stapler operation, including articulation and actuation of the tool assemblies.

SUMMARY

According to one aspect of the present disclosure, a surgical instrument is disclosed, which includes a microcontroller coupled to a memory, the microcontroller is configured to control the surgical instrument and a usage counter stored in the memory that is incremented when the surgical instrument is activated, wherein the microcontroller is further configured to prevent actuation of the surgical instrument when the usage counter is above a predetermined threshold.

According to another aspect of the present disclosure, a surgical instrument is disclosed, which includes a microcontroller coupled to a memory, the microcontroller is configured to control the surgical instrument and a sterilization counter stored in the memory that is incremented when the surgical instrument is sterilized, wherein the microcontroller is further configured to prevent actuation of the surgical instrument when the sterilization counter is above a predetermined threshold.

According to a further aspect of the present disclosure, a surgical instrument is disclosed, which includes at least one component including a component microcontroller is configured to store an identifier corresponding to the at least one component and a microcontroller coupled to a memory, the microcontroller is configured to control the surgical instrument and to authenticate the at least one component based on a response to a challenge request, wherein the response includes the identifier.

BRIEF DESCRIPTION OF THE DRAWINGS

Various embodiments of the subject instrument are described herein with reference to the drawings wherein.

DETAILED DESCRIPTION

Embodiments of the presently disclosed powered surgical instrument are now described in detail with reference to the drawings, in which like reference numerals designate identical or corresponding elements in each of the several views. As used herein the term "distal" refers to that portion of the powered surgical instrument, or component thereof, farther from the user while the term "proximal" refers to that portion of the powered surgical instrument or component thereof, closer to the user.

Figure 1:
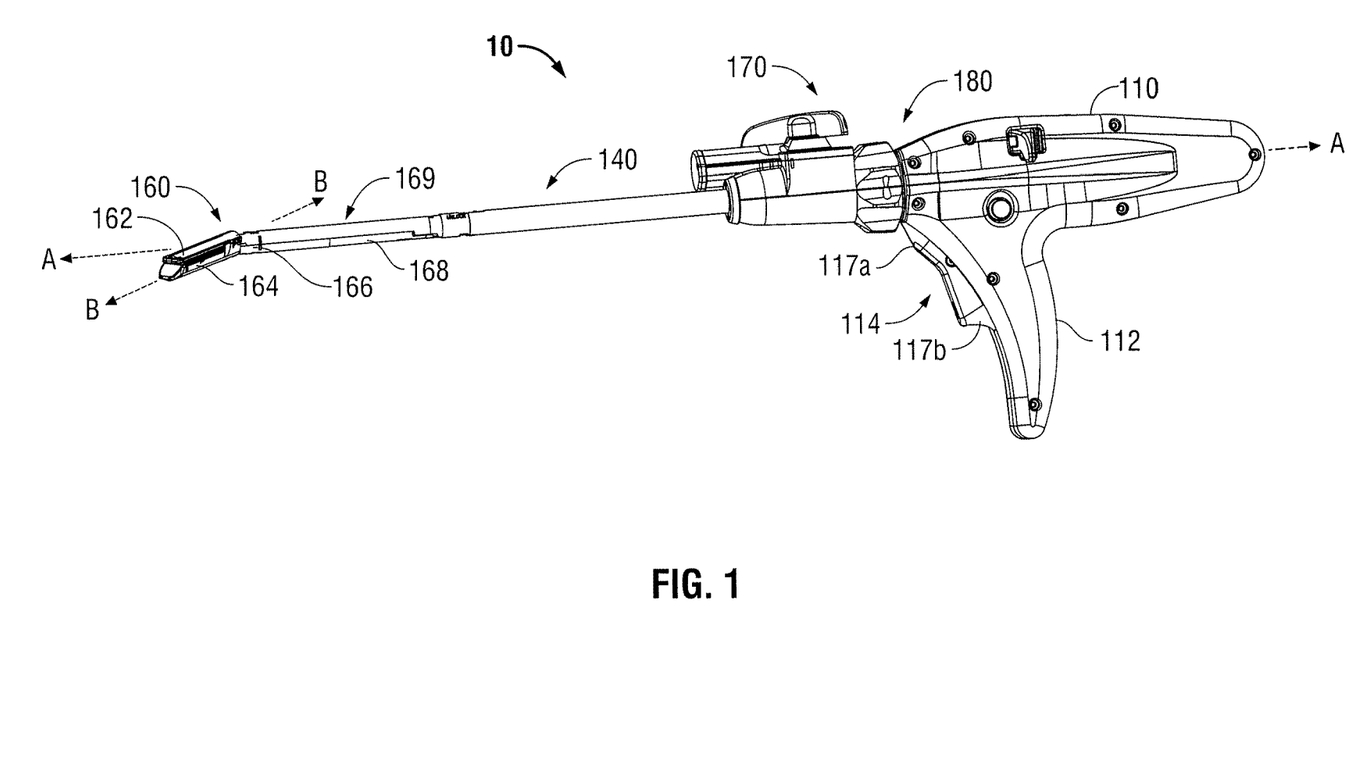
FIG. 1 is a perspective view of a powered surgical instrument according to an embodiment of the present disclosure.

A powered surgical instrument, e.g., a surgical stapler, in accordance with the present disclosure is referred to in the figures as reference numeral 10. Referring initially to FIG. 1, powered surgical instrument 10 includes a housing 110, an endoscopic portion 140 defining a first longitudinal axis A-A extending therethrough, and an articulating tool assembly (e.g., end effector 160), defining a second longitudinal axis B-B extending therethrough. Endoscopic portion 140 extends distally from housing 110 and the end effector 160 is disposed adjacent a distal portion of endoscopic portion 140. In an embodiment, the components of the housing 110 are sealed against infiltration of particulate and/or fluid contamination and help prevent damage of the components by sterilization processes.

According to an embodiment of the present disclosure, end effector 160 includes a first jaw member having one or more surgical fasteners (e.g., cartridge assembly 164) and a second opposing jaw member including an anvil portion for deploying and forming the surgical fasteners (e.g., an anvil assembly 162). In certain embodiments, the staples are housed in cartridge assembly 164 to apply linear rows of staples to body tissue either in simultaneous or sequential manner. Either one or both of the anvil assembly 162 and the cartridge assembly 164 are movable in relation to one another between an open position, in which the anvil assembly 162 is spaced from cartridge assembly 164, and an approximated or clamped position, in which the anvil assembly 162 is in juxtaposed alignment with cartridge assembly 164.

It is further envisioned that end effector 160 is attached to a mounting portion 166, which is pivotably attached to a body portion 168. Body portion 168 may be integral with endoscopic portion 140 of powered surgical instrument 10, or may be removably attached to the instrument 10 to provide a replaceable, disposable loading unit (DLU) or single use loading unit (SULU) (e.g., loading unit 169). In certain embodiments, the reusable portion may be configured for sterilization and re-use in a subsequent surgical procedure.

The loading unit 169 may be connectable to endoscopic portion 140 through a bayonet connection. It is envisioned that the loading unit 169 has an articulation link connected to mounting portion 166 of the loading unit 169 and the articulation link is connected to a linkage rod so that the end effector 160 is articulated as the linkage rod is translated in the distal-proximal direction along first longitudinal axis A-A as discussed in more detail below. Other means of connecting end effector 160 to endoscopic portion 140 to allow articulation may be used, such as a flexible tube or a tube comprising a plurality of pivotable members.

The loading unit 169 may incorporate or be configured to incorporate various end effectors, such as vessel sealing devices, linear stapling devices, circular stapling devices, cutters, graspers, etc. Such end effectors may be coupled to endoscopic portion 140 of powered surgical instrument 10. An intermediate flexible shaft may be included between handle portion 112 and loading unit. It is envisioned that the incorporation of a flexible shaft may facilitate access to and/or within certain areas of the body.

Figure 2:
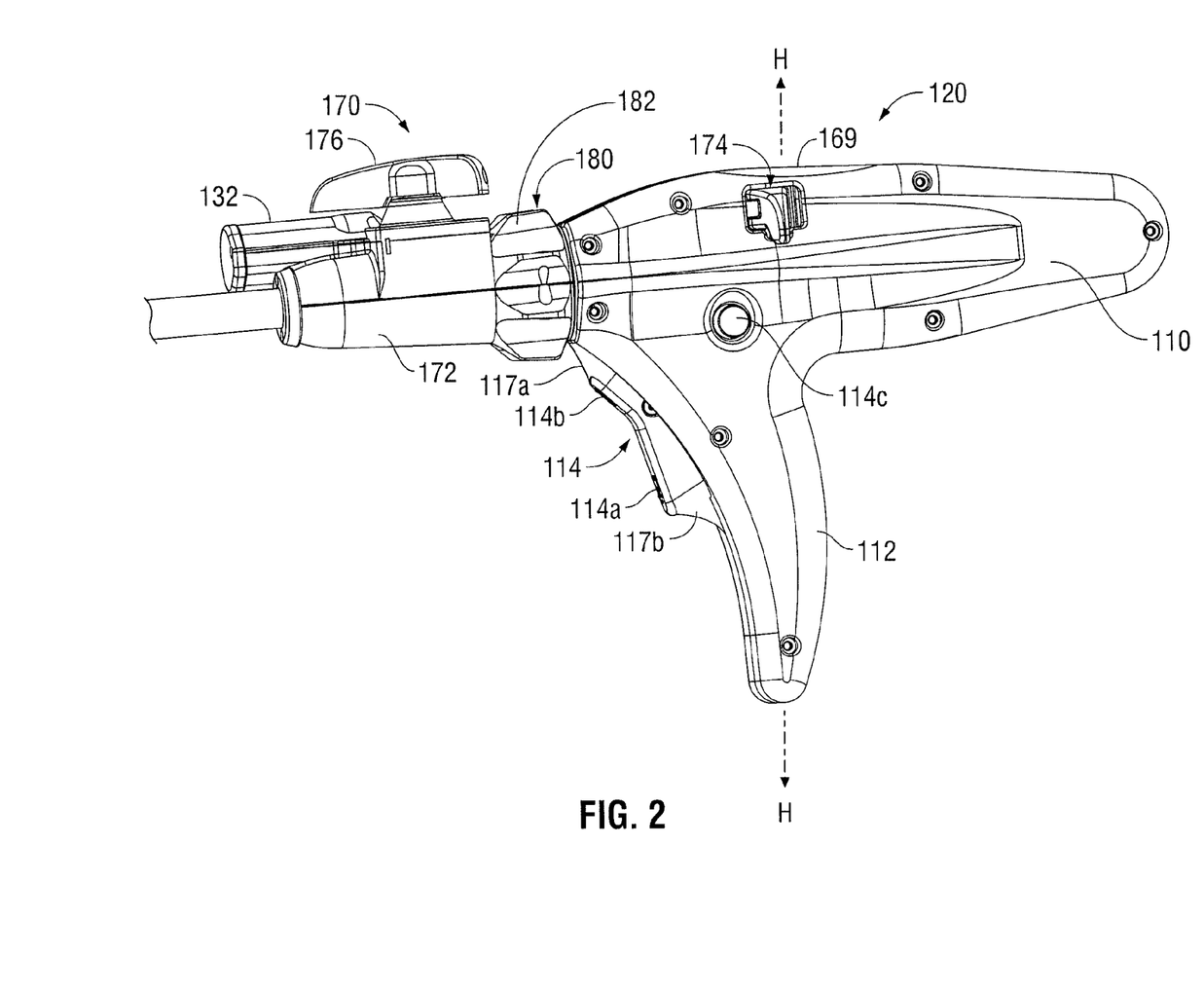
FIG. 2 is a partial enlarged perspective view of the powered surgical instrument of FIG. 1 according to the embodiment of the present disclosure.

With reference to FIGS. 1 and 2, an enlarged view of the housing 110 is illustrated according to an embodiment of the present disclosure. In the illustrated embodiment, housing 110 includes a handle portion 112 having a main drive switch 114 disposed thereon. The switch 114 may include first and second switches 114a and 114b formed together as a toggle switch. The handle portion 112, which defines a handle axis H-H, is configured to be grasped by fingers of a user. The handle portion 112 has an ergonomic shape providing ample palm grip leverage which helps prevent the handle portion 112 from being squeezed out of the user's hand during operation. Each switch 114a and 114b is shown as being disposed at a suitable location on handle portion 112 to facilitate its depression by a user's finger or fingers.

Figure 4:
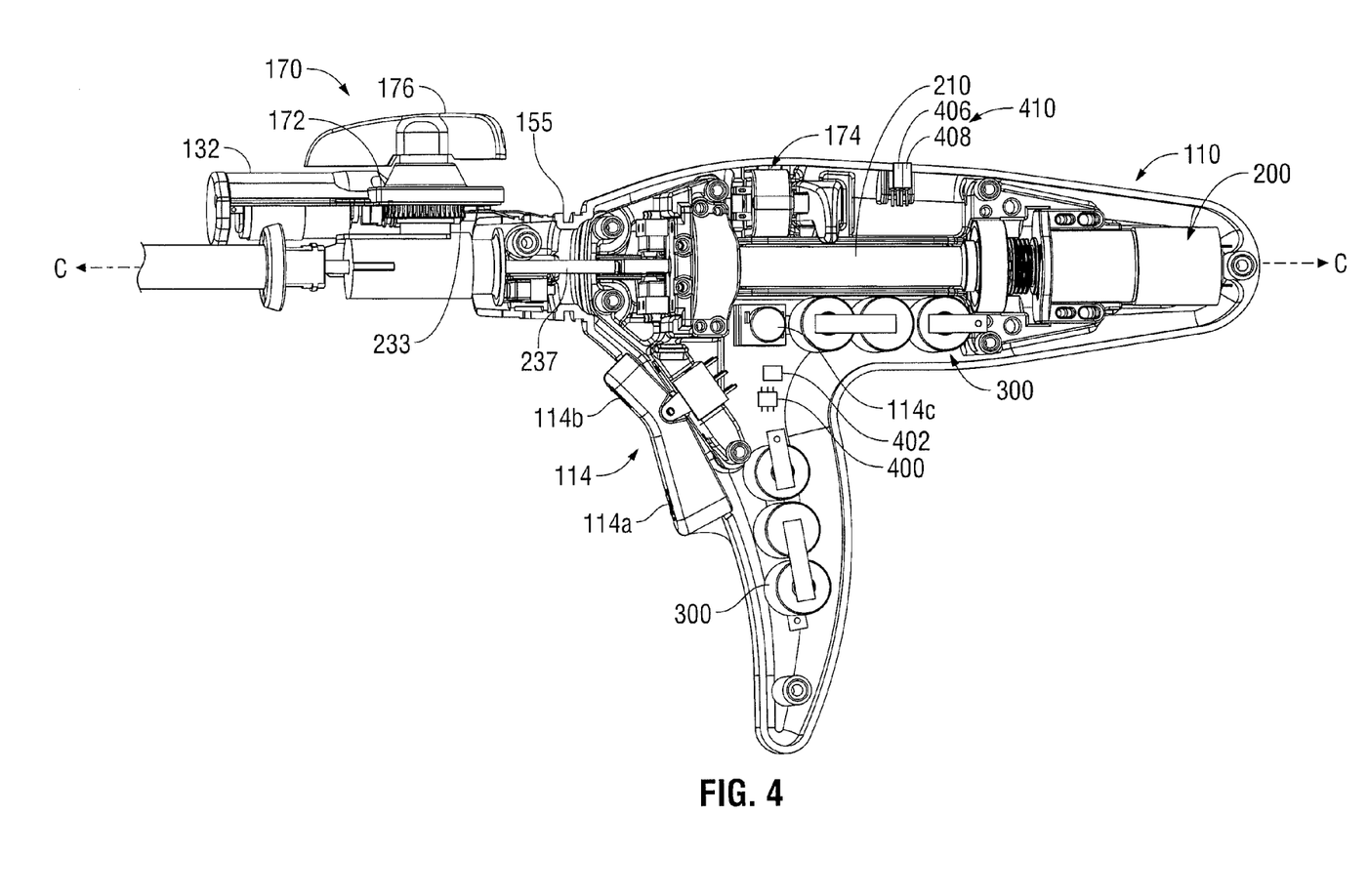
FIG. 4 is a partial perspective sectional view of internal components of the powered surgical instrument of FIG. 1 according to the embodiment of the present disclosure.

Additionally, and with reference to FIGS. 1 and 2, switches 114a, 114b may be used for starting and/or stopping movement of drive motor 200 (FIG. 4). In one embodiment, the switch 114a is configured to activate the drive motor 200 in a first direction to advance firing rod (not explicitly shown) in a distal direction thereby approximating the anvil and the cartridge assemblies 162 and 164. Conversely, the switch 114b may be configured to retract the firing rod to open the anvil and cartridge assemblies 162 and 164 by activating the drive motor 200 in a reverse direction. The retraction mode initiates a mechanical lock out, preventing further progression of stapling and cutting by the loading unit 169. The toggle has a first position for activating switch 114a, a second position for activating switch 114b, and a neutral position between the first and second positions.

The housing 110, in particular the handle portion 112, includes switch shields 117a and 117b. The switch shields 117a and 117b may have a rib-like shape surrounding the bottom portion of the switch 114a and the top portion of the switch 114b, respectively. The switch shield 117a and 117b prevent accidental activation of the switch 114. Further, the switches 114a and 114b have high tactile feedback requiring increased pressure for activation.

In one embodiment, the switches 114a and 114b are configured as multi-speed (e.g., two or more), incremental or variable speed switches which control the speed of the drive motor 200 and the firing rod in a non-linear manner. For example, switches 114a, 114b can be pressure-sensitive. This type of control interface allows for gradual increase in the rate of speed of the drive components from a slower and more precise mode to a faster operation. To prevent accidental activation of retraction, the switch 114b may be disconnected electronically until a fail safe switch 114c is pressed.

The switches 114a and 114b are coupled to a non-linear speed control circuit which can be implemented as a voltage regulation circuit, a variable resistance circuit, or a microelectronic pulse width modulation circuit. The switches 114a and 144b may interface with the control circuit by displacing or actuating variable control devices, such as rheostatic devices, multiple position switch circuit, linear and/or rotary variable displacement transducers, linear and/or rotary potentiometers, optical encoders, ferromagnetic sensors, and Hall Effect sensors. This allows the switches 114a and 114b to operate the drive motor 200 in multiple speed modes, such as gradually increasing the speed of the drive motor 200 either incrementally or gradually depending on the type of the control circuit being used, based on the depression of the switches 114a and 114b.

Figure 3:
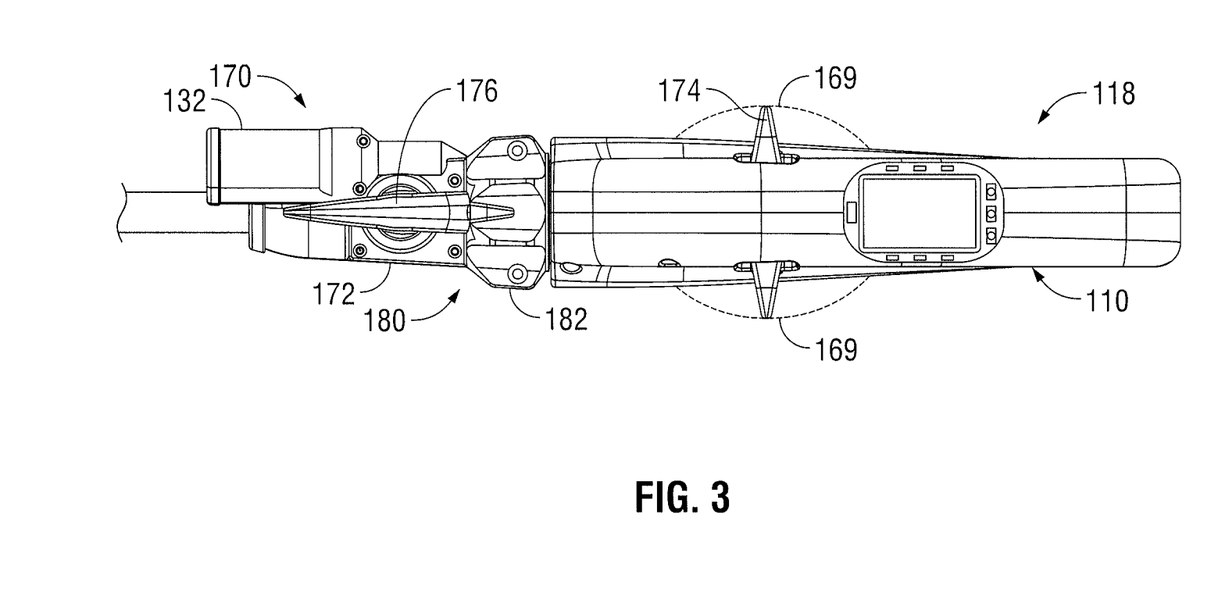
FIG. 3 is a partial enlarged plan view of the powered surgical instrument of FIG. 1 according to the embodiment of the present disclosure.

FIGS. 2-4 illustrate an articulation mechanism 170, including an articulation housing 172, a powered articulation switch 174, an articulation motor 132 and a manual articulation knob 176. Translation of the powered articulation switch 174 or pivoting of the manual articulation knob 176 activates the articulation motor 132 which then actuates an articulation gear 233 of the articulation mechanism 170 as shown in FIG. 4. Actuation of articulation mechanism 170 causes the end effector 160 to move from its first position, where longitudinal axis B-B is substantially aligned with longitudinal axis A-A, towards a position in which longitudinal axis B-B is disposed at an angle to longitudinal axis A-A. The powered articulation switch 174 may also incorporate similar non-linear speed controls as the clamping mechanism. These can be controlled by the switches 114a and 114b.

With reference to FIGS. 2 and 3, the housing 110 includes switch shields 169 having a wing-like shape and extending from the top surface of the housing 110 over the switch 174. The switch shields 169 prevent accidental activation of the switch 174 and require the user to reach below the shield 169 in order to activate the articulation mechanism 170.

Additionally, articulation housing 172 and powered articulation switch 174 are mounted to a rotating housing assembly 180. Rotation of a rotation knob 182 about first longitudinal axis A-A causes housing assembly 180 as well as articulation housing 172 and powered articulation switch 174 to rotate about first longitudinal axis A-A, and thus causes corresponding rotation of distal portion 224 of firing rod 220 and end effector 160 about first longitudinal axis A-A. The articulation mechanism 170 is electro-mechanically coupled to one or more conductive rings that are disposed on a housing nose assembly 155 (FIG. 4). The conductive rings may be soldered and/or crimped onto the nose assembly 155 and are in electrical contact with a power source 300 thereby providing electrical power to the articulation mechanism 170. The nose assembly 155 may be modular and may be attached to the housing 110 during assembly to allow for easier soldering and/or crimping of the rings. The articulation mechanism 170 may include one or more brush and/or spring loaded contacts in contact with the conductive rings such that as the housing assembly 180 is rotated along with the articulation housing 172 the articulation mechanism 170 is in continuous contact with the conductive rings thereby receiving electrical power from the power source 300.

Further details of articulation housing 172, powered articulation switch 174, manual articulation knob 176 and providing articulation to end effector 160 are described in detail in commonly-owned U.S. patent application Ser. No. 11/724,733 filed Mar. 15, 2007, the contents of which are hereby incorporated by reference in their entirety. It is envisioned that any combinations of limit switches, proximity sensors (e.g., optical and/or ferromagnetic), linear variable displacement transducers and shaft encoders which may be disposed within housing 110, may be utilized to control and/or record an articulation angle of end effector 160 and/or position of the firing rod 220.

As shown in FIG. 4, the instrument 10 also includes a microcontroller 400 electrically coupled to the motor 200 and various sensors disposed in the instrument 10. The sensors detect various operating parameters of the instrument 10 (e.g., linear speed, rotation speed, articulation position, temperature, battery charge, and the like), which are then reported to the microcontroller 400. The microcontroller 400 may then respond accordingly to the measured operating parameters (e.g., adjust the speed of the motor 200, control articulation angle, shut-off the power supply, report error conditions, etc.).

Figure 5:
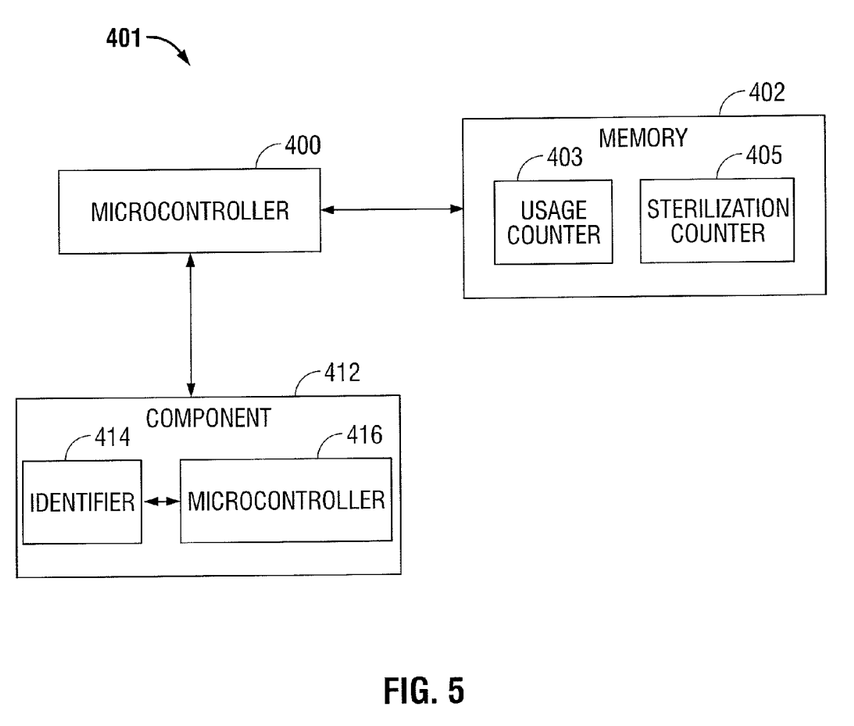
FIG. 5 is a schematic diagram of a controller circuit according to the embodiment of the present disclosure.

With reference to FIG. 5, a controller circuit 401 is shown. The controller circuit 401 includes the microcontroller 400 that is coupled to a memory 402 (e.g., non-volatile memory), which stores one or more software applications (e.g., firmware) for controlling the operation and functionality of the instrument 10. The microcontroller 400 processes input data from the user interface and adjusts the operation of the instrument 10 in response to the inputs. The adjustments to the instrument 10 may include powering the instrument 10 on or off, speed control by means of voltage regulation or voltage pulse width modulation, torque limitation by reducing duty cycle or pulsing the voltage on and off to limit average current delivery during a predetermined period of time.

In one embodiment, the microcontroller 400 and the memory 402 may be integrated into an application-specific integrated circuit ("ASIC") customized for control of the instrument 10. In another embodiment, the microcontroller 400 may be a one-time programmable ("OTP") microcontroller to prevent new code or firmware being written onto the microcontroller 400. The use of OTP and ASIC prevents unauthorized re-processors from rewriting the code controlling the instrument 10 and overriding the usage limitations discussed below.

It is envisioned that the instrument 10 may be used only a predetermined number of times. In other words, it is desirable to limit the number of reuses to a number mandated by the manufacturer or to ensure that a single-use instrument is only used once. With reference to FIG. 5, the microcontroller 400 is configured to maintain a usage counter 403 for counting the number of times the instrument 10 has been used. The usage counter 403 is stored in the memory 402. The microcontroller 400 may determine the number of uses based on the number of activations of the motor 200, the number of firing strokes performed by the motor 200, and length of operation for each activation. The usage counter 403 is initialized at zero prior to the instrument 10 being used for the first time and may not be reset by third parties. The usage counter 403 is incremented by the microcontroller 400 whenever the microcontroller 400 determines that the instrument 10 has been activated. In one embodiment, the usage counter 403 may be encrypted to prevent resetting of the counter 403. The usage counter 403 may also be a timer that records the time that the instrument 10 has been used. The total usage time is also recorded in the memory 402. Prior to activation of the instrument 10, the microcontroller 400 determines if the usage counter 403 is below a predetermined usage threshold. If the usage counter 403 exceeds the threshold, the microcontroller 400 prevents activation of the instrument 10.

In another embodiment, the microcontroller 400 is configured to maintain a sterilization counter 405 in the memory 402, if a certain number of re-uses of the instrument 10 are advised. The sterilization counter 405 may be implemented in conjunction with the usage counter 403. The sterilization counter 405 is also stored in the memory 402 and maintains a number of times the instrument 10 has been sterilized.

As shown in FIG. 4, the instrument 10 includes a sterilization sensor 410 (e.g., temperature sensor 406 and/or a moisture sensor 408), which detect when the instrument 10 has passed through a sterilization cycle. The temperature sensor 406 may be a thermistor, a thermopile, a thermocouple, a thermal infrared sensor, a resistance temperature detector, a linear active thermistor, a bimetallic contact switch, and the like. The moisture sensor 408 may be of capacitive, resistive and thermal conductivity types. The temperature and moisture sensors 406 and 408 are coupled to the microcontroller 400 and/or the memory 402 and are configured to increment the sterilization counter when the temperature and/or moisture are detected to be above predetermined thresholds (e.g., temperatures above 80° C. and humidity above 60%). The temperature and moisture sensors 406 and 408 may be integrated into the ASIC with the microcontroller 400 and the memory 402 to prevent tampering.

In another embodiment, the sterilization counter 405 may be encrypted to prevent resetting of the sterilization counter 405. Prior to activation of the instrument 10, the microcontroller 400 determines if the sterilization counter 405 is below a predetermined usage threshold. If the sterilization counter 405 exceeds the threshold, the microcontroller 400 prevents activation of the instrument 10.

With the modular design of the instrument 10, certain components 412 of the instrument 10 (e.g., motor 200, power source 300, loading unit 169, etc.) may be replaced during the life-time of the instrument 10. However, such modularity also provides unauthorized reuse of the instrument 10 by replacing the components 412. To prevent unauthorized replacement of the components 412, each of the components 412 may include an identifier 414 (FIG. 5) associated therewith. The identifiers 414 may be any value stored in a memory and/or component microcontroller 416 of the component that can be read by the microcontroller 400, such as a serial number. The microcontroller 416 may be coupled through wired and/or wireless communication protocols to the microcontroller 400 of the instrument 10 to authenticate the component 412. The identifier 414 may be encrypted to prevent unauthorized reading of the identifier. In another embodiment, the identifier may be a unique electrical measurable value of the component 412 (e.g., resistance, capacitance, inductance, etc.).

Figure 6:
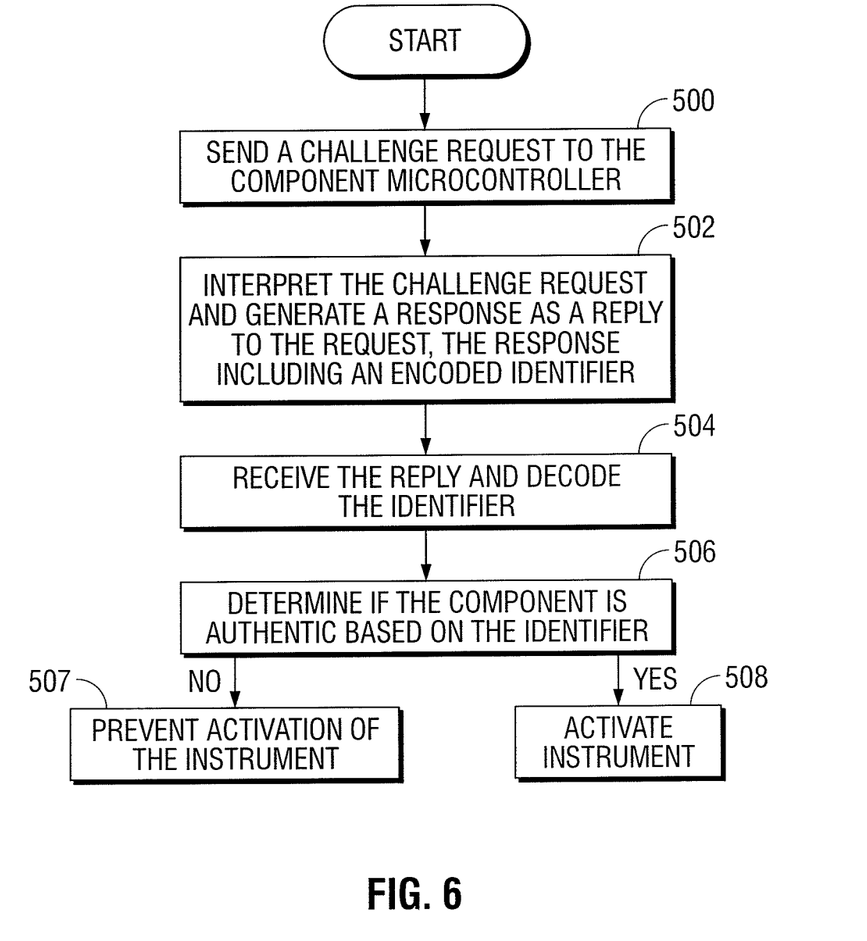
FIG. 6 is a flow chart of a method according to the embodiment of the present disclosure.

To ensure that only authorized components 412 are used in the instrument 10, the microcontroller 400 may execute a so-called challenge-response authentication algorithm as shown in FIG. 6. In step 500, the microcontroller 400 sends a challenge request to the component microcontroller 408. In step 502, the microcontroller 416 interprets the challenge request and generates a response as a reply to the request. The response includes the identifier 414 and may be encoded using a first pair of an encryption key that is specific to the microcontroller 416. In step 504, the microcontroller 400 receives the reply and decodes the identifier 414 using a second pair of the key. In step 506, the microcontroller 400 determines if the component 412 is authentic based on the identifier 414, by comparing the identifier 414 with a pre-approved list of authentic identifiers. If the identifier is not valid, in step 507, microcontroller 400 prevents activation of the instrument 10. If the identifier is valid, the process proceeds to step 508, the instrument 10 commences operation.

The above-discussed systems and method for controlling usage of the instrument 10 and components 412 thereof may be combined in a unitary authentication process. The usage counter 403, the sterilization counter 405 and the response to the authentication algorithm may be combined in a single value stored in the memory 402 as a so-called "device status word" ("DSW"). Upon power-up of the instrument 10, the microcontroller 400 checks the DSW to determine if the instrument 10 may be unlocked. This involves a determination whether the usage counter 403 and the sterilization counter 405 are below a predetermined usage threshold and whether all of the components 412 are authentic. In addition, an authentication flag may be set in the DSW that prevents activation of the instrument 10 if any of the components 412 are found to be inauthentic. If either the usage or the sterilization counters 403 and 405 are above the thresholds or the authentication flag is activated, the microcontroller 400 prevents activation of the instrument 10. The DSW may be continually updated prior to activation of the instrument 10. The DSW may also be encrypted to prevent unauthorized access and tampering.

It will be understood that various modifications may be made to the embodiments shown herein. Therefore, the above description should not be construed as limiting, but merely as exemplifications of preferred embodiments. Although specific features of the powered surgical instrument are shown in some of the drawings and not in others, this is for convenience only as each feature may be combined with any or all of the other features in accordance with the aspects of the present disclosure. Other embodiments will occur to those skilled in the art and are within the following claims.

What is claimed:

1. A surgical instrument, comprising:
   a housing;
   an endoscopic portion extending distally from the housing;
   an end effector coupled to the endoscopic portion;
   at least one motor disposed within the housing and including a motor microcontroller having stored thereon a unique identifier associated with the at least one motor;
   a memory device;
   an instrument microcontroller coupled to the memory device and configured to control the surgical instrument, the instrument microcontroller configured to send a challenge request to the motor microcontroller of the at least one motor to authenticate the at least one motor by comparing the unique identifier associated with the motor microcontroller of the at least one motor with a pre-approved set of identifiers;
   a sterilization counter stored in the memory device, and
   a sterilization sensor coupled to the instrument microcontroller, the instrument microcontroller configured to increment the sterilization counter when the sterilization sensor detects at least one of temperature or moisture above a predetermined threshold,
   wherein the unique identifier is a unique electrical, measurable value of the motor, the electrical, measurable value of the motor including a resistance, a capacitance, an inductance, or combinations thereof.

2. The surgical instrument according to claim 1, further comprising:
   a usage counter stored in the memory device and configured to be incremented in response to activation of the surgical instrument.

3. The surgical instrument according to claim 2, wherein the memory device includes a device status word that incorporates the usage counter, the sterilization counter and an authentication flag, the authentication flag configured to be activated based on a predetermined identifier.

4. The surgical instrument according to claim 3, wherein the device status word is encrypted.

5. The surgical instrument according to claim 3, wherein the instrument microcontroller is further configured to prevent actuation of the surgical instrument in response to at least one of the usage counter being above a predetermined threshold, the sterilization counter being above a predetermined threshold, or the authentication flag being activated.

6. The surgical instrument according to claim 1, wherein the surgical instrument is a surgical stapling instrument and the end effector includes an anvil assembly and a cartridge assembly, wherein the instrument microcontroller is electrically coupled to the motor.

7. The surgical instrument according to claim 6, wherein the motor is configured to cause the cartridge assembly and the anvil assembly to clamp together.

8. The surgical instrument according to claim 7, further comprising a usage counter stored in the memory device, wherein the usage counter is configured to be incremented when the motor is activated.

9. The surgical instrument according to claim 1, further comprising a loading unit including a body portion extending distally from the endoscopic portion, wherein the end effector is pivotably attached to the body portion.

10. The surgical instrument according to claim 9, wherein the loading unit includes a loading unit microcontroller.

11. The surgical instrument according to claim 1, wherein the motor microcontroller of the at least one motor is coupled to the instrument microcontroller through a wireless communication protocol.

12. The surgical instrument according to claim 1, wherein the housing includes a handle portion having a main drive switch configured to activate the motor.

13. The surgical instrument according to claim 1, wherein the sterilization sensor partially extends through an outer wall of the housing.

14. The surgical instrument according to claim 13, wherein the sterilization sensor includes a temperature sensor and a moisture sensor.

* * * * *